US008916150B2

(12) United States Patent
Soparkar

(10) Patent No.: US 8,916,150 B2
(45) Date of Patent: Dec. 23, 2014

(54) COMPOSITIONS AND METHODS FOR ENHANCING METAL ION DEPENDENT DRUG THERAPIES

(71) Applicant: Charles N. S. Soparkar, Houston, TX (US)

(72) Inventor: Charles N. S. Soparkar, Houston, TX (US)

(73) Assignee: CNSS IP Holdings, Inc., Houston, TX (US)

( * ) Notice: Subject to any disclaimer, the term of this patent is extended or adjusted under 35 U.S.C. 154(b) by 0 days.

(21) Appl. No.: 14/067,654

(22) Filed: Oct. 30, 2013

(65) Prior Publication Data

US 2014/0056869 A1 Feb. 27, 2014

Related U.S. Application Data

(62) Division of application No. 12/821,370, filed on Jun. 23, 2010, now Pat. No. 8,591,884.

(60) Provisional application No. 61/219,932, filed on Jun. 24, 2009.

(51) Int. Cl.

| | |
|---|---|
| ***A61K 38/48*** | (2006.01) |
| ***A61K 9/48*** | (2006.01) |
| ***A61K 47/00*** | (2006.01) |
| ***G01N 33/50*** | (2006.01) |
| ***A61K 39/08*** | (2006.01) |
| ***A61K 38/46*** | (2006.01) |
| ***A61K 33/30*** | (2006.01) |
| ***A23L 1/304*** | (2006.01) |

(52) U.S. Cl.

CPC ............ *A61K 33/30* (2013.01); *G01N 33/5088* (2013.01); *G01N 2800/709* (2013.01); *C12Y 304/24069* (2013.01); *A61K 39/08* (2013.01); *A61K 38/465* (2013.01); *A23L 1/3045* (2013.01); *A61K 38/4893* (2013.01); *A23L 1/304* (2013.01); *G01N 2800/52* (2013.01)

USPC ........ 424/94.67; 424/439; 424/451; 424/614; 424/643

(58) Field of Classification Search

USPC ....................... 424/94.67, 439, 451, 614, 643

See application file for complete search history.

(56) References Cited

U.S. PATENT DOCUMENTS

| | | | | |
|---|---|---|---|---|
| 5,696,077 | A | 12/1997 | Johnson et al. | |
| 5,770,217 | A * | 6/1998 | Kutilek et al. | 424/442 |
| 6,488,956 | B1 * | 12/2002 | Paradissis et al. | 424/439 |
| 6,585,993 | B2 | 7/2003 | Donovan et al. | |
| 7,189,541 | B2 | 3/2007 | Donovan | |
| 7,491,403 | B2 | 2/2009 | Borodic | |
| 2003/0118598 | A1 | 6/2003 | Hunt | |
| 2005/0214326 | A1 | 9/2005 | Hunt | |
| 2006/0269575 | A1 | 11/2006 | Hunt | |
| 2007/0269463 | A1 | 11/2007 | Donovan | |

FOREIGN PATENT DOCUMENTS

| | | | |
|---|---|---|---|
| EP | 0420358 | B1 | 5/1999 |
| WO | 98/30681 | | 7/1998 |
| WO | 99/49740 | | 10/1999 |
| WO | 2007/041664 | A1 | 4/2007 |

OTHER PUBLICATIONS

Dietary Reference Intakes, A Report of the Panel on Micronutrients., et al., "Zinc", National Academy of Sciences, pp. 442-501 (2001).

Ahmed, et al., "Factors Affecting Autocatalysis of Botulinum A Neurotoxin Light Chain", The Protein Journal, vol. 23 (7), pp. 445-451 (Oct. 2004).

Gallaher, et al., "Bioavailability of Different Sources of Protected Zinc", Trace Elements in Man and Animals 10, pp. 293-297 (2000).

Allen, Lindsay H., "Zinc and micronutrient supplements for children", The American Journal of Clinical Nutrition, Vol, 68 (suppl), pp. 495S-498S (1998).

Cai, et al., "Comparison of Extracellular and Intracellular Potency of Botulinum Neurotoxins", Infection and Immunity, vol. 74 (10), pp. 5617-5624 (Oct. 2006).

Dietary Reference Intakes (DRIs): Recommended Intakes for Individuals, Vitamins, by the National Academy of Sciences (2004).

Ward, et al., "Phytase assessment", Feedstuffs (May 28, 2007).

Foran, et al.,"Evaluation of the Therapeutic Usefulness Botulinum Neurotoxin B, C1, E, and F Compared with the Long Lasting Type A", The Journal of Biological Chemistry: vol. 278 (2), pp. 1363-1371, (Jan. 2003).

Gibson, et al., "Dietary interventions to prevent zinc deficiency", The American Journal of Clinical Nutrition, vol. 68 (suppl), pp. 484S-487S (1998).

Hambidge, et al., "Zinc Deficiency: A Special Challenge", The Journal of Nutrition, presented as part of the symposium "Food-Based Approaches to Combating Micronutrient Deficiencies in Children of Developing Countries", 2006 Experimental Biology meeting, pp. 1101-1105 (Apr. 3, 2006).

Lönnerdal, Bo, "Dietary Factors Influencing Zinc Absorption", The Journal of Nutrition, presented at the international workshop "Zinc and Health: Current Status and Future Directions", pp. 1378S-1383S (Nov. 4-5, 1998).

(Continued)

*Primary Examiner* — Rodney P Swartz

(74) *Attorney, Agent, or Firm* — Wong Cabello Lutsch Rutherford & Brucculeri, LLP

(57) ABSTRACT

Methods and compositions are provided for increasing responsiveness to therapeutic metalloproteases including increasing and/or maximizing responsiveness and preventing botulinum and tetanus toxin resistance due to a functional deficiency of zinc. Also provided are methods for zinc replacement or supplement in lacking individuals comprising the administration of a zinc supplement for a loading period and/or administration of a phytase supplement together with the zinc supplement. Also provided are methods for standardization of botulinum toxin potency assays that provide for greater certainty and margins of safety in the use of products from different manufacturers.

17 Claims, 3 Drawing Sheets

(56) References Cited

OTHER PUBLICATIONS

Martínez, et al., "Pharmacological Zinc and Phytase Supplementation Enhance Metallothionein mRNA Abundance and Protein Concentration in Newly Weaned Pigs", The Journal of Nutrition, presented in part at the 11th meeting of Trace Elements in Man and Animals (TEMA), pp. 538-544 (Jun. 2-6, 2002).
McAllister, et al., "Superactivation of the Botulinum Neurotoxin Serotype A Light Chain Metalloprotease: A New Wrinkle in Botulinum Neurotoxin", Journal of the American Chemical Society, vol. 128 (13), pp. 4176-4177 (Apr. 5, 2006).
Naik, et al., "Botulinum Toxin in Ophthalmic Plastic Surgery", Indian Journal of Ophthalmology, vol. 53, pp. 279-288 (2005).
Nutrient Requirements of Laboratory Animals, p. 91, 4th Revised Ed. (1995).
Lei, et al., "Supplemental Microbial Phytase Improves Bioavailability of Dietary Zinc to Weaning Pigs", The Journal of Nutrition, presented in part at the 84th Annual Meeting of the American Society of Animal Science, pp. 1117-1123 (Aug. 8-11, 1992).
Sandberg, et al., "Dietary *Aspergillus niger* Phytase Increases Iron Absorption in Humans", The Journal of Nutrition, American Institute of Nutrition (1996).
Schiavo, et al., "Botulinum Neurotoxins Are Zinc Proteins", The Journal of Biological Chemistry, vol. 267 (33), pp. 23479-23483 (Nov. 25, 1992).
Schiavo, et al., "Neurotoxins Affecting Neuroexocylosis", Physiological Reviews, vol. 80 (2), pp. 717-766, (Apr. 2000).
Sesardic, et al., "Alternatives to the LD50 assay for botulinum toxin potency testing: Strategies and progress towards refinement, reduction and replacement", AATEX 14, Special Issue, Proc. 6th World Congress on Alternatives & Animal Use in the Life Sciences, pp. 581-585 (Aug. 21-25, 2007).
Sheth, Parul R., "Toxins to drugs: The case of botulinum toxin", Current Science, vol. 95 (8), pp. 1009-1011, (Oct. 25, 2008).
Simpson, et al., "The Role of Zinc Binding in the Biological Activity of Botulinum Toxin", The Journal of Biological Chemistry, vol. 276 (29), pp. 27034-27041 (Jul. 20, 2001).
USDA National Nutrient Database for Standard Reference, Release 20, pp. 1-25 (Oct. 2007).
Frueh, Bartley, et al., "Treatment of Blepharospasm With Botulinum Toxin", Arch Ophthalmol, vol. 102, pp. 1464-1468 (1984).
Wang, Jiafu, et al., "Novel Chimeras of Botulinum Neurotoxins A and E Unveil Contributions from the Binding, Translocation, and Protease Domains to Their Functional Characteristics", Journal of Biological Chemistry, vol. 283 (25), pp. 16993-17002 (Jun. 20, 2008).
Maret, Wolfgang, et al., "Zinc requirements and the risks and benefits of zinc supplementation", Journal of Trace Elements in Medicine and Biology 20, pp. 3-18 (2006).
Hoffman, Robert O., et al., "Botulinum in the Treatment of Adult Motility Disorders", Int Ophthalmol Clin 26, pp. 241-250 (1986).
Ao, T et al. "Effects of organic zinc and phytase supplementation in a maize-soybean meal diet on the performance and tissue zinc content ot broiler chicks", British Poultry Science, vol. 48(6), pp. 690-695 (Dec. 2007).
International Search Report and Written Opinion regarding corresponding patent application No. PCT/US2010/039674, dated Nov. 10, 2010.

* cited by examiner

*Figure 1*

| | | | | Placebo | | | Zinc 10 | | | Zinc 50 + P | | |
|---|---|---|---|---|---|---|---|---|---|---|---|---|
| ID | SEX | AGE | DZ | $D_P$ | $E_P$ | $T_P$ | $D_{Z10}$ | $E_{Z10}$ | $T_{Z10}$ | $D_{Z50P}$ | $E_{Z50P}$ | $T_{Z50P}$ |
| 1 | M | 39 | BH | | | | | | | 0 | 1 | B |
| 2 | M | 56 | BH | | | | | | | 0.23 | 2 | B |
| 3 | M | 71 | BH | 0 | 0 | B | | | | 0.15 | 2 | B |
| 4 | M | 76 | BH | | | | | | | 0.12 | 2 | B |
| 5 | M | 78 | BH | 0.07 | 1 | B | 0.07 | 1 | B | 0.23 | 3 | B |
| 6 | F | 68 | BH | | | | | | | 0.12 | 0 | B |
| 7 | F | 70 | BH | | | | 0 | 0 | B | 0.23 | 2 | B |
| 8 | F | 71 | BH | | | | -0.15 | 0 | B | 0.23 | 2 | B |
| 9 | F | 73 | BH | | | | | | | 0.23 | 2 | B |
| 10 | F | 73 | BH | 0 | -1 | B | | | | 0.16 | 2 | B |
| 11 | F | 73 | BH | -0.07 | 0 | M | 0 | 1 | M | 0.23 | 2 | M |
| 12 | F | 76 | BH | | | | | | | 0.31 | 3 | B |
| 13 | F | 76 | BH | | | | | | | 0.31 | 2 | B |
| 14 | F | 77 | BH | -0.06 | 0 | M | 0.07 | 1 | M | 0.16 | 2 | M |
| 15 | F | 77 | BH | | | | | | | 0.35 | -2* | B |
| 16 | F | 77 | BH | | | | | | | 0.23 | 0 | B |
| 17 | F | 80 | BH | | | | | | | 0.35 | 3 | B |
| 18 | F | 80 | BH | 0.06 | -1 | B | 0 | 0 | B | 0.16 | 2 | B |
| 19 | F | 82 | BH | | | | | | | 0 | 2 | B |
| 20 | F | 84 | BH | 0 | 0 | B | | | | 0.07 | 2 | B |
| 21 | F | 84 | BH | | | | 0.07 | 1 | B | 0.23 | 3 | B |
| 22 | F | 85 | BH | | | | | | | 0.23 | 2 | B |
| 23 | F | 88 | BH | 0.07 | 1 | B | 0 | 0 | B | 0.23 | 2 | B |
| 24 | F | 58 | BC | | | | | | | 0.31 | -2* | B |
| 25 | F | 61 | BC | | | | | | | 0.15 | 2 | B |
| 26 | F | 63 | BC | 0 | 0 | B | 0 | 0 | B | 0.23 | -2* | B |
| 27 | M | 72 | H | | | | | | | 0.31 | 2 | B |
| 28 | F | 65 | H | | | | 0 | 0 | B | 0.47 | 2 | B |
| 29 | F | 38 | C | | | | | | | 0.47 | 2 | B |
| 30 | F | 43 | C | | | | | | | 0.31 | 2 | B |
| 31 | F | 54 | C | 0 | 0 | B | 0 | 0 | B | 0.23 | 2 | B |
| 32 | F | 57 | C | | | | | | | 0.15 | 1 | B |
| 33 | M | 43 | H | | | | | | | 0.33 | 1 | B |
| 34 | M | 47 | H | | | | | | | 0.5 | 0 | B |
| 35 | F | 64 | BC | 0 | 0 | B | | | | 0.23 | 2 | B |
| 36 | F | 69 | BC | 0 | 0 | B | 0.12 | 1 | B | 0.31 | 3 | B |
| 37 | M | 73 | BC | 0 | 0 | B | 0 | 0 | B | 0.23 | 2 | B |
| 38 | M | 74 | BC | 0 | 1 | B | 0 | 0 | B | 0.23 | 2 | B |
| 39 | F | 35 | C | 0 | 0 | B | | | | 0.25 | 2 | B |
| 40 | F | 39 | C | 0 | 0 | B | 0 | 1 | B | 0.25 | 1 | B |
| 41 | F | 43 | C | 0 | 0 | B | | | | 0 | 1 | B |
| 42 | F | 44 | C | | | | | | | 0.25 | 1 | D |
| 43 | F | 56 | C | | | | | | | 0.31 | 2 | D |
| 44 | M | 52 | C | | | | | | | 0.31 | 1 | D |

COMPOSITIONS AND METHODS FOR ENHANCING METAL ION DEPENDENT DRUG THERAPIES

CROSS REFERENCE TO RELATED APPLICATION

This application is a divisional of U.S. application Ser. No. 12/821,370 filed Jun. 23, 2010, now U.S. Pat. No. 8,591,884, which claims priority to U.S. provisional application No. 61/219,932, filed Jun. 24, 2009, which applications are incorporated herein by reference in their entireties.

FIELD OF THE INVENTION

This invention relates generally to compositions and methods used in conjunction with assay and administration of certain pharmaceutics, in particular, co-factor dependent toxins such as the Clostridial neurotoxins.

BACKGROUND OF THE INVENTION

Without limiting the scope of the invention, its background is described in connection with the development of lethal toxins such as botulinum toxin into useful pharmaceuticals. The disease term "botulism" was derived from the Latin word for sausage, botulus, on the basis of a fatal outbreak in Germany in the 1800s caused by partially cooked sausage. Botulism was later determined to be due to toxins elaborated by the *Clostridium botulinum* organism, originally isolated in 1895. *C. botulinum* is a gram-positive, spore-forming, anaerobic rod commonly found on plants, in soil, water, and the intestinal tracts of animals. Botulinum toxin was first purified in 1928 and is among the most toxic substances known. Botulinum toxins act to cause paralysis at four different sites in the body: the neuromuscular junction, autonomic ganglia, postganglionic parasympathetic nerve endings, and postganglionic sympathetic nerve endings that release acetylcholine (Ach).

Several different strains of *Clostridium*, including *C. butyricum, C. baratii*, and *C. argentinense*, have been identified that produce antigenically distinct forms of pharmacologically similar botulinum neurotoxins (abbreviated either as BTX or BoNT). Eight major serotypes of botulinum neurotoxins elaborated by bacteria of the *Clostridium* genus are now known: A, B, C (C1 and C2), D, E, F, and G. Subtypes of the serotypes may be closely related or more distant. For example BoNT-A1 and A2 are 95% homologous while BoNT-A3 and A4 are respectively 81% and 88% homologous to BoNT-A1. Botulinum toxin type A (BoNT-A) is the most potent toxin, followed by the B and F toxin types. It is these types that have been exploited commercially to date.

BoNT-A (Oculinum, now BOTOX® brand, Allergan, Inc.) was FDA approved in 1989 for medical treatment of blepharospasm (uncontrolled blinking), strabismus (crossed eyes), Meige's syndrome (bilateral blepharospasm with concurrent dystonia of the lower face), and hemifacial spasm. Approval to treat cervical dystonia, a neurological movement disorder causing severe neck and shoulder contractions was received in December 2000. BOTOX® was approved in the UK for axillary hyperhidrosis (excessive sweating) in 2001 and, in the same year, BOTOX® was approved in Canada for axillary hyperhidrosis, focal muscle spasticity, and cosmetic treatment of wrinkles at the brow line. In 2002, the U.S. FDA announced the approval of BOTOX® Cosmetic to temporarily improve the appearance of moderate-to-severe frown lines between the eyebrows (glabellar lines). In July 2004, the FDA approved BOTOX® to treat primary axillary hyperhidrosis.

BoNT-B has also been developed for clinical use and several products are currently commercially available (e.g., MyoBloc® in the United States and NeuroBloc® in Europe, Solstice Neurosciences). MyoBloc® was FDA approved in 2000 for treatment of cervical dystonia. BOTOX® BoNT-A is considered to be 50-100 times more potent than Myobloc® BoNT-B for any given specific treatment.

A number of different manufacturers worldwide are now producing purified BoNT-A under various brand names including Xeomin® (Merz Pharma, Germany), Prosigne® (Lanzhou Inst. For Biol. Prod., China), and Neuronox® (Meditoxin® in Korea, Medy-Tox, Inc., Korea). As with other biological products, the biological activity for new batches must be determined. This is particularly critical for drugs such as botulinum toxin, which have considerable toxicity and for which restoration of normal neuromusclar activity is prolonged. Botulinum toxin delivered intramuscularly acts at the neuromuscular junction to cause muscle paralysis by inhibiting the release of Ach from presynaptic motor neurons. The peak of the paralytic effect occurs 4-7 days after injection. Approximately 2 months after the administration of botulinum toxin, the axon begins to expand, and new nerve terminal sprouts emerge and extend towards the muscle surface. These new nerve sprouts re-establish the motor nerve unit and muscle paralysis is reversed typically within 2-4 months. Overdose is sufficiently critical and recovery sufficiently prolonged that an antivenin is available in the case of accidental overdose.

Doses of all commercially available botulinum toxins are expressed in terms of units of biologic activity. One unit of botulinum toxin corresponds to the calculated median intraperitoneal lethal dose ($LD_{50}$) in mice. See Hoffman R O, Helveston E M. "Botulinum in the treatment of adult motility disorders" *Int Ophthalmol Clin* 26 (1986) 241-50. Although certainly not ideal, the $LD_{50}$ assay has been retained due to its high sensitivity. The definition of unit applies to all forms of commercially available toxins, in spite of the fact that a standardized approach to potency testing has not been adopted and inter-manufacturer differences in mouse $LD_{50}$ assay protocols have led to considerable variability in the per unit activity for different products. For example, the bio-equivalence ratio of the Dysport® brand of BoNT-A (Ipsen Pharmaceuticals, France) to Botox® has been suggested to be between 2.5:1 and 4:1 by various studies in patients with blepharospasm and hemifacial spasm. As a consequence, when communicating recommended botulinum toxin dosage in particular indications, it is has been considered important to specify the particular brand of toxin being used because the units used in labeling are product specific and non-interchangeable. Further complications arise due the fact that BoNT is a large and relatively labile molecule. Proper reconstitution of the product is important and shelf life is quite limited.

Botulinum toxin is capable of inducing formation of antibodies in humans leading to decreased effect of the toxin over time. See Frueh B R, et al. "Treatment of Bepharospasm with Botulinum Toxin. A preliminary report" *Arch Ophthalmol* 102 (1984) 1464. Antibody production is thought to be a function of cumulative dose, antigenic load per dose, and time interval between injections. Thus, it has been suggested that the smallest therapeutic dose be given with maximum time interval between sequential injections. Given the importance of the use of BoNT in treating certain diseases, use of BoNT-F is under investigation in patients who have become immunologically resistant to serotypes A and B.

Although the botulinum toxins are effective for the majority of patients, therapeutic effect can vary widely independent of detectable antibody formation—not only from individual to individual, but also for an individual from treatment to treatment. Further, some populations have been identified to be more likely to show poor- or non-responsiveness to the toxins. For example, up to 30% of patients over the age of 65 may demonstrate decreased botulinum toxin efficacy. The basis of failure of a patient to respond to treatment can be difficult to discern, given that possible explanations include original manufacturer differences in potency, the possibility that the patient has developed toxin specific antibodies, as well as the possibility that the product has degraded or been agitated during reconstitution. However, diminished effect within a particular patient population suggests the possibility of another factor as well.

Reports of patient demise from the putative dose-dependent distant spread of very large amounts of botulinum toxin administration have surfaced in the last few years, so any methods which may decrease the dose of toxin necessary to achieve a desired therapeutic outcome would be beneficial.

From the foregoing, it is apparent that any ability to assure maximal patient responsiveness in treatment and to provide closer standardization of potency would represent an important therapeutic and safety advance.

BRIEF SUMMARY OF THE INVENTION

The present inventor has surprisingly found that administration of relatively high amounts of well absorbed forms of zinc prior to, concurrently with, or shortly following therapeutic administration of botulinum toxin will enable responsiveness to the toxin in individuals who were previously poorly responsive, and apparently enhance the functional potency of botulinum toxins in other individuals as well. Even more remarkable, the present inventor has found that zinc loading prior to administration of botulinum toxin increased responsiveness in virtually every individual tested. It thus appears clear that the tested individuals were previously relatively functionally deficient in zinc available for binding and activation of the botulinum toxin's light chain (LC) zinc dependent endopeptidase. Because the group of individuals who are at increased risk for zinc insufficiency as it relates to maximum responsiveness to the effects of botulinum toxin potentially include a large percentage of the patient population (See Table 1), the present finding provides several means for maximal possible zinc dependent responsiveness to botulinum toxin.

TABLE 1

| Risk Factors for Zinc Deficiency |
|---|
| 1. Diet |
| a. Vitamin supplements |
| i. Poorly absorbed (inexpensive) inorganic zinc forms |
| ii. Iron |
| iii. Vitamin A |
| iv. Calcium |
| v. Copper |
| b. High phytate intake |
| i. Whole grain breads and fiber |
| ii. Whole wheat products |
| iii. Cereals |
| iv. Soy |
| v. Oats |
| vi. Legumes (including peanuts, peanut butter, peas) |
| vii. Beans |
| viii. Corn |
| ix. Rice |
| x. Many pre-prepared foods (preservatives) |
| xi. Most beverages (including virtually all carbonated soft drinks) |
| 1. Phosphate containing compounds |
| 2. Preservative E391 |
| c. Alcohol consumption |
| i. Decreases Zinc absorption |
| ii. Increases urinary excretion |
| iii. Many wines contain phytates |
| d. Milk-based products containing casein and calcium |
| e. Many "fiber enriching" foods and supplements |
| f. Vegetarianism (diets low in red meats, poultry, and fish, but high in soy) |
| g. Foods containing EDTA preservative |
| 2. Medical conditions |
| a. Infections (viral, bacterial, fungal) |
| b. Burns |
| c. Most chronic illnesses |
| d. Malabsorption |
| i. Frequent Diarrhea |
| ii. Sprue, etc |
| iii. Constipation with frequent fiber and/or laxative use |
| 3. Pregnancy |
| 4. Age <25 or >65 |
| 5. Diuretic Use |

In certain aspects disclosed herein, the finding is extended to maximizing effectiveness of treatment with any compound that is dependent for activity on the availability of metal ions in the tissue being treated. In one embodiment, the compound is a therapeutic protease. In one embodiment, the therapeutic protease is a zinc endopeptidase, examples of which include botulinum toxin (BoNT), tetanus neurotoxin (TeNT), and Lyme Disease toxin (LDT) among others.

In one aspect, a method of preparing a subject for therapeutic compound administration is provided that includes instructing administration (via oral consumption or any other desired method) of a metal ion supplement for a loading period prior to—and in some cases concurrently with or shortly following—the administration of the compound, wherein the instructed administration of the metal ion supplement is at a sufficient level to eliminate a relative functional deficiency of the metal ion as a cause for poor responsiveness to the administered compound. In one aspect, the compound is a zinc endopeptidase such as a botulinum toxin. The metal ion can be in an inorganic or organic form but is ideally selected on the basis of sufficient bioavailability according to bioavailability measures known in the art.

In one aspect, a zinc supplement is provided that includes an organic zinc form selected from one or more of a zinc proteinate, a zinc chelate and/or salt with an organic molecule, and a zinc amino acid complex. The zinc supplement is designed to deliver 10 to 400 mg daily of elemental zinc. In other embodiments, the zinc supplement delivers 30 to 50 mg daily of elemental zinc.

In further aspects, metal ion absorption is promoted by instructing the patient to limit consumption of phytates during the loading period. In one particular embodiment, the subject is further instructed to administer, e.g., to orally consume, at least one phytase together with the metal ion supplement.

In one embodiment for maximizing responsiveness to therapeutic botulinum, tetanus neurotoxin, or lyme toxin and related chimeric or synthetic toxins, loading of zinc stores prior to, concurrently with, or shortly following treatment with the therapeutic metal ion dependent toxin is facilitated by the provision of a pre-procedure prep pack that includes a quantity of zinc supplements in capsule, powder, liquid, liquid-gel, liposomal suspension, or tablet form, wherein the zinc supplements are sufficient to supply 10 to 400 mg of elemental zinc daily for a loading period prior to treatment of a patient with a toxin together with instructions directing the patient to take the zinc supplements and reduce intake of phytates. In other aspects of this embodiment, the pre-procedure prep pack further includes a quantity of phytase supplements in capsule, powder, liquid, liquid-gel, liposomal suspension, or tablet form and in sufficient quantity for administration together with the zinc supplements through the loading period.

In another embodiment of the invention, methods of potency testing of toxins including botulinum toxins are provided that enable a measure of standardization across the industry. For these embodiments, oral or parenteral zinc supplementation is administered to test animals for a loading period prior to or simultaneous with toxin potency testing, wherein the zinc supplement has been determined to provide sufficient zinc to maximize responsiveness to administered toxin. Maximum responsiveness is determined empirically by testing diets or zinc supplementation for maximum responsiveness including by modulating the level of zinc supplementation together with maximizing zinc absorption. Zinc absorption can be modulated by controlling dietary phytate levels as well as by adding phytase to the diet.

In another embodiment of the invention, zinc is supplied to the tissue by topical cream, or local or systemic injection. In other aspects, reconstitution of therapeutic toxins in a zinc-containing solution is provided for purposes of insuring the presence of adequate zinc for maximal activity of the toxin in the target tissues.

In another embodiment of the invention, zinc and phytase in combination are used to safely and effectively rapidly increase whole body zinc levels in times of medical need, including, but not limited to, conditions such as wound healing, burn recovery, immune compromise, and male impotency.

The methods and compositions of the present disclosure provide a remedy for botulinum toxin relative resistance and therapeutic variability in many individuals with a resulting greatly improved therapeutic outcome, margin of safety, and reliability of therapeutic effect from treatment to treatment. Maximization of the potential effectiveness of administered therapeutic metallopeptidases allows for administration of lower doses and longer times between readministration in some patients with a putative attendant lower risk of the development of antibody mediated resistance and a potential decrease in distant spread of the toxin with undesired effects. The methods for standardization of botulinum toxin potency assays herein provided resolve a long standing problem in the industry and provide for greater certainty and margins of safety in the use of products from different manufacturers.

BRIEF DESCRIPTION OF THE DRAWINGS

For a more complete understanding of the present invention, including features and advantages, reference is now made to the detailed description of the invention along with the accompanying figures:

FIG. 1 depicts the raw data of a trial of supplementation of zinc and zinc plus phytase for four days prior to administration of therapeutic botulinum toxin.

DETAILED DESCRIPTION OF THE INVENTION

Figure 2:
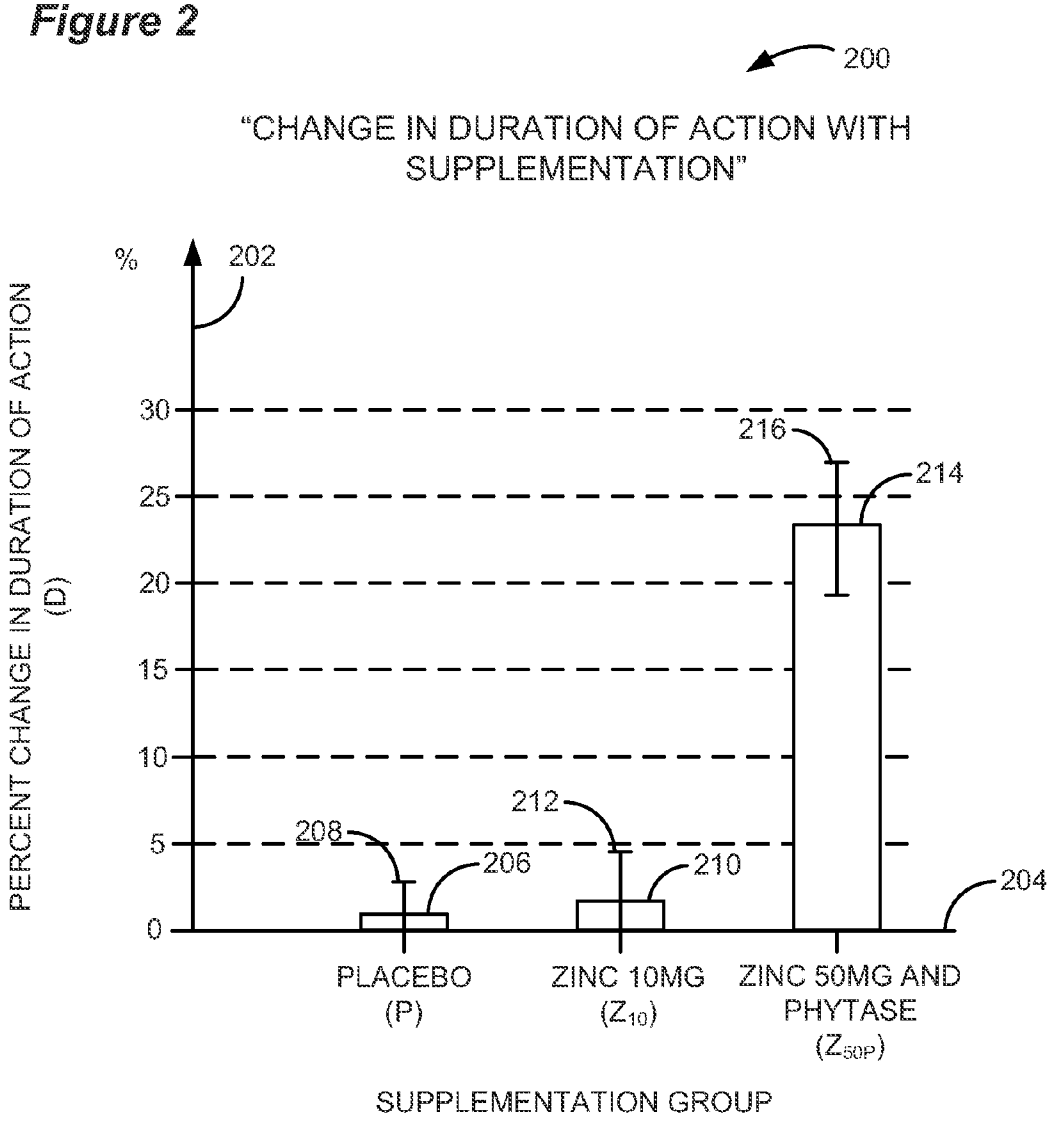
FIG. 2 depicts the graphic results of the trial of supplementation of zinc and zinc plus phytase for four days prior to the administration of therapeutic botulinum toxins with respect to the duration of the toxin's effect in the patient.

While the making and using of various embodiments of the present invention are discussed in detail below, it should be appreciated that the present invention provides many applicable inventive concepts which can be employed in a wide variety of specific contexts. The specific embodiments discussed herein are merely illustrative of specific ways to make and use the invention and do not delimit the scope of the invention.

Variability of botulinum toxin action in certain individuals has heretofore been attributed to different sources or lots of the toxin, improper reconstitution or storage, variations in injection technique, the use of topical anesthetics and/or cooling agents, and antibody mediated resistance. The present inventor considered that botulinum toxin resistance might have a basis in an insufficiency of available zinc and has proven this remarkable hypothesis. This finding provides a remedy for botulinum toxin resistance in many individuals with a resulting greatly improved therapeutic outcome and margin of safety. The finding is extendable to enhancing responsiveness of individuals to other administered compounds that are active in vivo on the basis of metal ion availability including other enzymes such as tetanus and lyme toxins, as well as other conditions wherein a patient may benefit from increased whole body zinc levels, such as wound healing, burn recovery, immune compromise, and male impotency. Also provided are methods for standardization of toxin potency assays that provide for greater certainty and margins of safety in the use of products from different manufacturers.

The term "therapeutic metallopeptidase" as used herein refers to a peptidase administered for therapeutic purposes that requires a metal ion for partial or full activity. Examples include the zinc dependent metalloprotease neurotoxins botulinum toxin and tetanus toxin, both of which inhibit neurotransmitter release.

As used herein the term "Clostridial toxin" refers to isolated zinc metalloprotease neurotoxins natively produced by Clostridial species including without limitation *Clostridium tetani, Clostridium botulinum, Clostridium butyricum* and *Clostridium beratti*, as well as Clostridial neurotoxins made recombinantly including in other microbial genera and species. The term "botulinum toxin" refers to botulinum toxin serotypes A, B, C, E, F and G, and subtypes thereof, whether natively produced by Clostridial species or made recombinantly. Also included as "botulinum toxins" are isolated botulinum toxin chains (heavy or light chains), whether isolated from Clostridial species or generated recombinantly. The term "botulinum toxin" also includes novel recombinant chimeras. For example, novel recombinant chimeras have been generated between BoNT-A and E and certain of these forms have enhanced activity over native forms. See e.g. Wang, J. et al. "Novel chimeras of botulinum neurotoxins A and E unveil contributions from the binding, translocation, and protease domains to their functional characteristics" *J. Biol. Chem.* 283 (2008) 16993-17002.

As used herein, the term "toxin injection" refers to the introduction of a toxin at a site where therapeutic effect is desired and should also encompass the concepts of other toxin delivery systems, including, but not limited to, topical toxin application, site-directed release of systemically administered toxin, or nanosystem delivery vehicles.

The botulinum toxins are natively produced in *Clostridium* bacteria as relatively inactive, single polypeptide chains of about 150 kDa weight with a high degree of amino acid sequence homology among the toxin types. The single polypeptide is subsequently cleaved into a roughly 100 kDa heavy chain (HC) and a 50 kDa light chain (LC). The HC and LC chains are finally bound together by disulfide bonds to form a heterodimer. The botulinum toxin HC is responsible for toxin binding to and translocation into neurons involved in neuromuscular activity. Once inside the neuron, the toxin LC moiety inhibits neurotransmitter release by proteolytically cleaving various SNARE (Soluble N-ethylmaleimide-sensitive factor Attachment protein Receptor) proteins involved in the release of acetylcholine at the neuromuscular junction, thus inhibiting muscular contraction in response to neuronal stimulation. The LC proteolytic activity is located at the N-terminus of the LC and functions as a zinc-dependent endopeptidase.

At the neuromuscular junction, the mechanism of BoNT action involves three steps, binding, internalization, and inhibition of neurotransmitter release through inactivation of various of the SNARE proteins. Three SNARE proteins, syntaxin 1, SNAP-25, and synaptobrevin (a.k.a. vesicle-associated membrane protein or VAMP) together form the metastable "trans" SNARE complexes that act to dock the synaptic vesicle to the presynaptic membrane.

The SNARE protein targets of the LC endopeptidase differ between certain of the BoNT serotypes. SNAP-25 is synaptosome-associated presynaptic membrane protein required for fusion of neurotransmitter-containing vesicles and is the target for BoNT-A and E. VAMP is the target for BoNTs B, D, F and G. The proteolytic target for BoNT-C1 is the syntaxin membrane protein.

Tetanus neurotoxin (TeNT) is also produced by bacteria of the genus *Clostridium* and, as with BoNT, is a 150 kDa protein consisting of three domains. However, after binding to the motoneuron presynaptic membrane, TeNT is internalized and transported retroaxonally to the spinal cord. It is then exported out of the motor neuron cell bodies and internalized by presynaptic nerve terminals, where it acts by cleaving VAMP/synaptobrevin thereby preventing release of the inhibitory transmitter glycine. Synaptic transmission onto motor neurons is predominantly inhibitory. As such, prevention of this inhibition results in hyperactivity of affected motor neurons and thus results in spastic paralysis by the unregulated contraction (tetany) of the innervated muscles. Although not yet clinically available, TeNT has been proposed as potentially useful for treatment of neurological conditions of the CNS.

As previously mentioned, the Clostridial neurotoxins are zinc dependent metalloproteases. When active, BoNT contains one $Zn^{2+}$ (divalent cation zinc) per molecule. Zinc may be bound to the botulinum toxin LC before or after entry into cells but is critical for endopeptidase activity. In vitro studies have shown that spontaneous loss of zinc from toxin sites is relatively slow, but may be increased with longer time in solution. If the endopeptidase becomes inactive by loss of bound zinc, addition of exogenous zinc can reactivate the toxin.

Dietary Supplementation to Provide Adequate Levels of Metal Ions Required for Activity of Metalloproteases.

Until the early 1960s, it was believed that zinc deficiency in humans did not occur. Since then, it has been determined that zinc is an essential trace element and that zinc deficiency is common. Zinc has been found relatively recently to be required for the catalytic activity of hundreds of enzymes and that cells have a tight regulatory apparatus for $Zn^{2+}$ availability, which is indicative of its importance in cellular metabolism. Intracellular zinc ($Zn^{2+}$) is in homeostasis with zinc binding proteins such as the metallothionein-1 (MT-1) family of proteins, which act to control the concentration of free $Zn^{2+}$ by sequestering and releasing $Zn^{2+}$ when required. However, the dynamics of binding and release of $Zn^{2+}$, the cellular distribution of $Zn^{2+}$, and the homeostatic control of $Zn^{2+}$ are not well understood.

Clinically relevant zinc deficiency results in growth retardation, loss of appetite, and impaired immune function as well as weight loss, delayed healing of wounds, taste abnormalities, and mental lethargy. In severe cases, which are largely found in underdeveloped countries, zinc deficiency causes hair loss, diarrhea, delayed sexual maturation, impotence, hypogonadism in males, and eye and skin lesions. While overt zinc deficiency is rare in developed countries, zinc deficiency is common in developing countries where cereals constitute a very large part of the diet.

Based on studies of patients with overt symptoms in developing countries, it was found that phytates in cereals markedly inhibit absorption of zinc, iron, and other divalent cations. Phytates, mostly inositol hexaphosphates and pentaphosphates, are found in abundance in the whole grain breads and fiber, whole wheat products, cereals, soy, oats, legumes (including peanuts and peas), corn, rice, and many food products touted as rich in fiber. The phosphate groups of these carbocyclic polyols form strong and insoluble complexes with zinc and inhibit its absorption.

Subclinical zinc deficiency is difficult to detect. Laboratory measurement of zinc nutritional status is difficult due to its distribution throughout the body as a component of various metalloproteins and other zinc binding proteins, as well as nucleic acids. Measurement of levels of zinc in the body is difficult, and serum or plasma levels of zinc and rates of urinary excretion do not correlate well with intracellular or tissue zinc levels. See Maret W, Sandstead H H. "Zinc requirements and the risks and benefits of zinc supplementation." *J Trace Elem Med Biol* 20 (2006) 3-18. Furthermore, clinical effects of zinc deficiency can be present in the absence of abnormal laboratory findings. Thus, for clinical assessment of zinc deficiency, risk factors such as inadequate caloric intake, alcoholism, and digestive diseases are considered (Table 1) together with symptoms of zinc deficiency when determining a need for zinc supplementation.

Daily oral intake of zinc is required to maintain a steady state level due to a lack of a specialized zinc storage system. Dietary zinc is absorbed mostly through the small intestine. Increased consumption of foods with a high content of absorbable zinc can remedy overt zinc deficiency. Daily zinc losses have been calculated to be in the order of 0.63 mg/day for adult healthy men and 0.44 mg/day for adult healthy women. U.S. surveys indicate that the average intake of zinc in the U.S. is 14 mg/day in adult men and 9 mg/day is adult women. The Recommended Daily Allowance for oral zinc is 8 mg/day for adult (non pregnant or lactating) women and 11 mg/day in adult men. In contrast, the Daily Value (DV) for zinc is 15 mg daily. DVs were developed by the U.S. Food and Drug Administration to help consumers compare the nutrient contents of products in the context of a total diet. The DV for zinc is 15 mg for adults and children age 4 or older. The Tolerable Upper Intake Level (UL) for zinc has been set by the USDA at 40 mg/day. Gastrointestinal distress has been reported at doses of 50 to 150 mg/day over prolonged periods. An emetic dose of zinc is estimated to be 225 to 450 mg of zinc. Importantly, just 0.26 grams of phytate may inhibit the absorption of up to 50 mg of oral zinc, and, under medical supervision, patients may be given in excess of 200 mg/day of zinc supplementation.

Zinc is highly correlated with the protein content of foods but is more available in animal proteins than in protein rich plant foods. For example, although turkey (140 grams contains 4.34 mg of zinc) and chicken (140 grams contains 2.88 mg of zinc) are reasonably good sources of zinc, a 120 gram piece of tofu only contains 0.77 mg of zinc. The content of zinc in animal proteins varies widely. For example, 6 medium oysters provide 77 mg of zinc or over 500% of the RDA. In contrast, 3 ounces of beef shanks provide 8.9 mg of zinc.

Many individuals are at risk for subclinical zinc deficiency including those who take zinc supplementation but with less well absorbed inorganic forms or in combination with phytates that render the zinc unavailable. The present inventor has surprisingly found that prior administration of relatively high amounts of well absorbed forms of zinc will enable responsiveness to botulinum toxin in individuals who were previously poorly responsive. Clearly then, such individuals were likely previously functionally deficient in zinc available for binding and activation of the botulinum toxin LC zinc dependent endopeptidase. However, none of these individuals exhibited overt signs of zinc insufficiency.

Individuals who are at increased risk for zinc insufficiency as it relates to maximum responsiveness to the effects of botulinum toxin potentially include a large percentage of the patient population (See Table 1). Persons with potentially increased risk for zinc insufficiency in the present context include those who have diets rich in phytates (salts of phytic acid) which are found in whole grain breads and fiber, whole wheat products, cereals, soy, oats, legumes (including peanuts and peas), beans, corn, and rice. Also at risk are persons having diets low in beef, turkey, chicken, or oysters (i.e. vegetarians) or individuals who consume these high zinc foods together with foods and compounds that render the zinc unavailable including foods and other compounds high in phytic acid or phosphates.

Many foods and beverages contain phosphates or phytic acid as a preservative. Phytic acid (myo-inositol-1,2,3,4,5,6-hexakisphosphate, which has the formula $C_6H_6(OPO(OH)_2)_6$) is the primary storage form of phosphorus in many plant tissues including bran and seeds. Phytic acids are highly reactive and readily form complexes with mineral such as $Ca^{2+}$, $Fe^{2+/3+}$, $Mg^{2+}$, $Mn^{2+}$, $Cu^{2+}$ and $Zn^{2+}$, as well as with carbohydrates and proteins. Due to the ability to chelate divalent cations, phytic acids are among the compounds used to treat hard water, to remove iron and copper from wines, and to inactivate trace-metal contaminants in animal and vegetable oils. The preservative E391 is phytic acid.

As used herein, a "zinc supplement" means one or more forms of inorganic or organic zinc or combinations thereof for oral administration, including in solid, gel, liposomal and liquid forms. The term inorganic zinc refers to the divalent cation $Zn^{2+}$ and inorganic salts of zinc. Non-limiting examples include zinc chloride ($ZnCl_2$), tetrabasic zinc chloride ($Zn_5Cl_2(OH)_8$), zinc oxide (ZnO), zinc sulfate ($ZnSO_4$), and tetrabasic zinc chloride ($Zn_5Cl_2(OH)_8$). The percentage of elemental zinc varies in these forms. For example, approximately 23% of zinc sulfate consists of elemental zinc. Thus, 220 mg of zinc sulfate contains 50 mg of elemental zinc.

As used herein, the term "organic zinc" refers to organic zinc complexes as well as zinc proteinates, zinc chelates and salts with organic molecules and compounds, and zinc amino acid complexes including zinc histidine, zinc methionine (ZnMet), Zinc lysine (ZnLys) complexes, etc. Further non-limiting examples include zinc acetate ($Zn(O_2CCH_3)_2$), zinc ascorbate ($C_{12}H_{14}ZnO_{12}$), zinc aspartate ($C_8H_{10}N_2O_8Zn_2H$), zinc butyrate ($Zn(C_4H_7O_2)$), zinc carbonate ($ZnCO_3$), zinc citrate ($Zn_3(C_6H_5O_7)_2$), zinc gluconate ($Zn(C_{12}H_{22}O_{14})$), zinc glycinate ($C_4H_8N_2O_4Zn$), zinc histidinate ($C_{12}H_{16}N_6O_4Zn$), zinc ketoglutarate ($C_5H_4O_5Zn$), zinc lactate ($Zn(C_3H_5O_3)_2$), zinc malate ($C_4H_4O_5Zn$), zinc picolinate ($C_{12}H_8N_2O_4Zn$), zinc propanoate ($C_6H_{10}O_4Zn$), zinc stearate ($C_{36}H_{70}O_4Zn$), and zinc succinate ($C_4H_4O_4Zn$). As with inorganic zinc salts, the percentage of elemental zinc varies in these forms. For example with zinc arginate, 300 mg supplies 30 mg of elemental zinc.

Certain forms of zinc such as zinc oxide and zinc carbonate are essentially insoluble in aqueous solution and have been generally considered to be poorly absorbed. Single dose administration of 50 mg of zinc in the readily absorbed forms of zinc sulfate and zinc acetate induces nausea and vomiting in human adults, while the same dose of zinc oxide causes such symptoms in only a small percentage of individuals, presumably on the basis of differences in absorption. See Allen L H. "Zinc and Micronutrient Supplements For Children" *Am J CLin Nutr* 68 (Suppl) (1998) 4955. Thus, consideration of adequate dosages of dietary zinc for purposes of the present invention includes considerations of relative rates of absorption.

As used herein, the term "phytase" refers to hydrolase enzymes that are able to catalyze the release of phosphorus from phytic acid and salts thereof (phytates). Phytases are available from many sources including plant sources, generally from germinating seeds, and microbes. Phytases have been described derived from bacteria such as *Bacillus subtilis* and *Pseudomonas* species as well as from yeasts and filamentous fungi. The cloning and expression of the phytase gene from *Aspergillus niger* has been described among others. See EP0420358. Phytases fall into different types depending on the position specificity of their action phytic acid molecules. Thus, for example, a 3-phytase (myo-inositol hexaphosphate 3-phosphohydrolase, EC 3.1.3.8) first hydrolyses the ester bond at the 3-position. A 6-phytase (myoinositol hexaphosphate 6-phosphohydrolase, EC 3.1.3.26) first hydrolyzes the ester bond at the 6-position. Although there are exceptions, plant phytases are generally 6-phytases. Microbial phytases are mainly 3-phytases.

Frequent, long term alcohol consumption is associated with impaired zinc absorption and increased urinary excretion. Other potential risk factors for functional zinc deficiency include persons who take supplements that interfere with zinc absorption including iron, vitamin A, copper and calcium supplements; frequently consume milk based products containing casein; have infections, burns, or have recently had surgery; have any chronic illness; have frequent diarrhea or any malabsorption syndrome; are pregnant and/or are below the age of 25 or over the age of 70.

Given that the risk factors for a functional zinc deficiency in the present context are so common, one of the most expedient methods for assuring that sufficient zinc will be available for binding to and activation of botulinum toxin is to augment zinc stores by oral supplement administration prior to, concurrent with, or shortly following administration of the botulinum toxin. In one aspect of the invention, oral supplements and instructions for their use are provided. In one embodiment, the oral supplements include sufficient zinc to provide from 10 to 400 mg daily of elemental zinc. The amount of zinc administered varies with the relative absorpsion of the form of zinc selected, and well absorbed forms are given in lower doses to avoid emetic effects. Zinc at a level of 10 mg is essentially an RDA level of zinc. Particularly, in the lower end of the range of 10 to 400 mg of elemental zinc, co-administration of a phytase at a level of 0.8 to 10,000 units is preferably provided for ingestion at the time (i.e., within a couple of hours) of zinc ingestion in order to prevent phytic acid chelation of the ingested zinc. In one embodiment, phytase is provided for ingestion together with each zinc ingestion, as well as further phytase supplements to be taken with every meal in order to maximize availability of zinc from all dietary sources. In one embodiment, a high zinc loading dose is provided, which supplies from 30-100 mg elemental zinc daily together with 0.8-10,000 units of phytase.

Other Co-Preparation Methods for Augmenting the Effects of Administered Metalloproteases:

The present inventor has demonstrated that responsiveness to botulinum toxin can be dramatically improved by a period of zinc loading prior to administration of the toxin. This finding indicates that even in persons having a normal western diet and with no apparent evidence of zinc insufficiency, available zinc is limited at least as it relates to the activity of exogenously added metalloproteases that are zinc dependent for activity. In one embodiment, zinc is administered locally to the tissue that is to be treated with a Clostridial neurotoxin. In one aspect, a zinc solution is injected into sites for toxin injection at around the time of toxin injection, i.e. before, during and/or after toxin injection or toxin topical administration. In other aspects, zinc is administered in a penetrating cream that is applied topically to sites for toxin injection at around the time of toxin injection, i.e. before, during and/or after toxin injection. In other aspects, zinc is administered through the use of nanodelivery systems. In other aspects, zinc is administered via sublingual administration, nasal spray, eye drops, enemas, "forced air," transdermally, or rectal administration of any form, including a liposomal suspension or nanodelivery system. In further aspects, a zinc solution may be used to reconstitute the therapeutic toxins. Where larger areas or inaccessible areas are to be treated, or to more accurately dose the zinc therapy, zinc loading by intravenous or intramuscular injection may be alternatively employed.

Clostridial Neurotoxin Reconstitution Solutions:

Removal of $Zn^{2+}$ from the light chain (LC) by displacement in vitro with soluble chelators such as ethylenediaminetetraacetate (EDTA) completely abolishes enzymatic activity in cell free or broken cell preparations. However, toxin stripped of its bound zinc can retain activity against intact neuromuscular junctions, presumably because the internalized toxin is able to bind available cytosolic $Zn^{2+}$. See Simpson L L, et al. "The Role of Zinc Binding in the Biological Activity of Botulinum Toxin" *J Biol Chem* 276 (29) (2001) 27034-41. Although tissue that has been pretreated with chelators loses its ability to restore activity to toxin that has been stripped of zinc, addition of a molar excess of $Zn^{2+}$ (20 uM) to the tissue will rapidly restore the activity of zinc depleted toxin. Id.

Studies have shown that zinc does not provide a cryoprotectant or cryopermissive effect in lyophilization of botulinum toxin. See Allergan patent application Ser. No. 10/976,529, published as US 2005/0214326 and PCT/US2006/038913, published as WO 2007/041664. It was asserted in Allergan U.S. patent application Ser. No. 10/976,529, published as US 2005/0214326, that addition of zinc to lyophilization solutions does provide some increased potency and enhanced anti-microbial activity. However, further independent studies have shown that the LC of BoNT-A undergoes autocatalytic fragmentation during purification and storage and that this fragmentation is enhanced by zinc chloride, as well as other chlorides of divalent metals. On this basis, some have recommended that the toxin be stored frozen in a low concentration of neutral or higher pH that is devoid of any metals. Ahmed S A, et al. "Factors Affecting Autocatalysis of Botulinum A Neurotoxin Light Chain" *Protein J.* 23 (7) (2004) 445-51.

In any event, presently commercially available BoNT pharmaceutical compositions lack added $Zn^{2+}$ either prior to lyophilization or as an additive to a reconstitution solution. For example, BOTOX® brand BoNT-A available from Allergan, Inc. (Irvine, Calif.) consists of purified BoNT-A that has been purified from culture by a series of acid precipitations into a crystalline complex consisting of the active high molecular weight toxin protein and an associated hemagglutinin protein. The crystalline complex is re-dissolved in a solution containing saline and Human Serum Albumin (HSA) and sterile filtered (0.2 microns) prior to vacuum-drying. BOTOX® is reconstituted with sterile, preservative free 0.9% sodium chloride (saline) prior to intramuscular injection. Other commercially available BoNT pharmaceutical compositions include the Dysport® (Ipsen Ltd., Berkshire, U.K.) brand BoNT-A hemagglutinin complex, which is dried into a powder with HSA and lactose, to be reconstituted with saline before use. MyoBloc® brand BoNT-B is provided as in single use vials of an injectable solution of 5,000 U Botulinum Toxin Type B in complex with hemagglutinin and nonhemagglutinin proteins in 0.05% HSA, 0.01M sodium succinate, and 0.1M sodium chloride at about pH 5.6. Thus, activity of the BoNT must rely on whatever zinc remains bound to the molecule throughout purification and storage as well as $Zn^{2+}$ in host tissues for activity.

The results presented herein show that, in most individuals tested, zinc loading prior to treatment resulted in improved—sometimes dramatically improved—effects and duration of effects of the treatment. This shows that there is insufficient $Zn^{2+}$ bound to the toxin molecules for maximal activity and further shows that the tissues of normal individuals lack sufficient available $Zn^{2+}$ to compensate for lack of sufficient $Zn^{2+}$ bound to the molecules. Thus, in one embodiment presented herein, a BoNT reconstitution solution is provided that includes sufficient $Zn^{2+}$ to enable maximum responsiveness of the injected toxin by overcoming any deficiencies in either toxin bound zinc or tissue resident available zinc. Given the findings disclosed herein, an ideal level of $Zn^{2+}$ to be provided in reconstitution solutions for delivery can be determined empirically. In one embodiment, mouse neurotoxin potency assays are utilized to determine levels and forms of zinc to be added to the delivery solutions. In one embodiment, the mice are placed on a zinc deficient diet for a clearing period prior to testing of desired levels of $Zn^{2+}$ to be supplied in delivery formulations. By placing the mice in a state of relative zinc deficiency prior to testing, the contribution of $Zn^{2+}$ present in the delivery solution can be isolated. In one embodiment of the invention, the BoNT is lyophilized without added $Zn^{2+}$ and a reconstitution solution is provided that contains sufficient added $Zn^{2+}$ for maximal activity. In one embodiment, the $Zn^{2+}$ is present in the reconstitution solution at a concentration of from 10-400 μM.

In one embodiment, a reconstitution solution is provided that includes isotonic saline, i.e., approximately 0.9% or 0.155M NaCl in sterile aqueous solution (preserved or non preserved), and further includes elemental $Zn^{2+}$ at a concentration of from about 10 to about 50 μM or about 0.000065 g to about 0.00032 g/100 ml of elemental zinc. This quantity of elemental zinc can be provided, for example, with $ZnCl_2$ at about 0.000136 g to about 0.00068 g/100 ml.

Clostridial Neurotoxin Potency Assays:

The currently accepted assay of potency per vial for botulinum toxin is an intraperitoneal mouse lethal dose (MLD50)

assay. Potency can refer to recovered potency of the botulinum toxin after reconstitution or the potency of the botulinum toxin prior to lyophilization. One unit (U) of a botulinum toxin is defined as the amount of botulinum toxin which, upon intraperitoneal injection, kills 50% of a group of female Swiss Weber mice weighing 17-22 grams each at the start of the assay. Further specifics of the assay are provided in PCT/US2006/038913, published as WO 2007/041664, and incorporated herein by reference.

The European Pharmacopoeia (Ph Eur) monograph on Botulinum toxin type A (BoNT/A) for injection (01/2005:2113) has supported the use of alternative non-lethal and ex vivo methods to replace the mouse LD50 assay, subject to their validation. (Secardia, D. and Das, R. G. "Alternatives to the LD50 assay for botulinum toxin potency testing: Strategies and progress towards refinement, reduction and replacement" *AATEX* 14, *Special Issue,* 581-585. *Proc. 6th World Congress on Alternatives & Animal Use in the Life Sciences*. Aug. 21-25, 2007, Japan). Proposed alternative potency assays include the mouse flaccid paralysis assay (also known as the mouse abdominal ptosis assay), which relates the activity of BoNT/A to the degree of abdominal bulging seen after the toxin is subcutaneously injected into the left inguinocrural region of a mouse. The magnitude of the paralysis is dose-dependent. As only a sublethal dose of BoNT is injected, the assay is considered to be 10-fold more sensitive than the LD50 assay. The paralysis endpoint is more similar to the clinical use of the toxin because it evaluates localized muscle effects, rather than systemic toxicity. The flaccid paralysis assay is more rapid than the lethality test and provides results in 24 to 48 hours, compared to 72 to 96 hours for a typical LD50 assay.

An alternative ex vivo assay has also been proposed and measures the amplitude of a twitch response to electrical stimulation of an excised nerve/muscle preparation. The potency of the toxin determines the decrease in the amplitude of the twitch response. The usual endpoint of the assay is the time until a 50% decrease in amplitude is observed. The ex vivo model can provide results within two hours.

Although the $LD_{50}$ assay has been retained due to its high sensitivity, the assay is not standardized, and units used in labeling are product specific and not interchangeable. Absence of standardized testing is a safety issue given the extreme toxicity and slow recovery from overdosage. The present inventor has determined that oral administration of zinc results in considerable improvement in botulinum responsiveness in many patients that do not otherwise exhibit any indicia of zinc deficiency. This remarkable finding has been extended to botulinum potency assays and provides for maximum responsiveness in the test system. In one aspect, a standardized diet is provided to the mice for a period of time prior to conducting an intraperitoneal $LD_{50}$ assay, a mouse flaccid paralysis assay or an ex vivo twitch response assay.

A typical research grade rodent diet includes from 14-20% protein and 50 to over 70% carbohydrate. The highest percentage ingredients in the diet are high in phytates or otherwise inhibit zinc absorption. These include casein, corn starch, soybean meal, cellulose and may further include corn and/or soybean oils. Mineral mixtures are added to the diet but this is not standardized and can vary by 10 fold in different standard diets.

In various reported studies, diets containing 25-55 mg of zinc per kg of chow were considered adequate, while diets containing <1-5 mg of zinc per kg were considered deficient. In other reports, zinc values have been given in parts per million (ppm) and zinc deficient and adequate diets contained 1.5 and 70-75 ppm of zinc, respectively. It has been noted that a diet containing 10 mg/kg of zinc may be adequate where the primary protein source is egg white or casein but that at least 20 mg/kg would be required where a high phytate protein source such as soybean is used. Mice are relatively resistant to zinc toxicity and have been reported to not show significant effects from 500 mg Zn/L of water for up to 14 months.

In one embodiment of a method for normalizing Clostridial neurotoxin potency testing in animals and utilizing animal tissues, animals to be used for potency testing are placed on a defined diet designed to maximize available zinc for at least one week prior to testing. In one embodiment the diet is low in phytates and high in zinc. In one embodiment where a low phytate diet is given, the zinc level is at least two-fold in excess of recommended zinc levels. In one embodiment, a phytase is added to the diet in addition to a zinc level at least two-fold in excess of recommended levels. In one embodiment, the defined diet is selected by comparison of the potency of the same lot of Clostridial neurotoxin in groups of animals fed different diets for at least one week prior to the potency analysis. The diet providing the greatest sensitivity to the effects of the toxin is selected and standardized as the required defined diet for all future potency tests.

The following examples are included for the sake of completeness of disclosure and to illustrate the methods and compositions of the present invention as well as to present certain characteristics of the compositions. In no way are these examples intended to limit the scope or teaching of this disclosure.

Example 1

Reversal of Botulinum Toxin Resistance by Dietary Zinc Supplementation

The present inventor reasoned that differences in available intracellular zinc stores in individuals might explain the lack of botulinum responsiveness in some patients. In an initial exploration of the hypothesis, zinc supplementation was provided by food sources. Turkey was selected as a dietary source of bioavailable $Zn^{2+}$ on the basis of safety, low cost, easy accessibility, and general acceptance. The amount of turkey that the patients were directed to consume was calculated to provide a daily dose of 40 mg, or approximately 2.5 times the recommended daily value. A number of these patients were considered to be poorly responsive to botulinum toxins such that control of their blepharospasm symptoms had been historically difficult to achieve. The results showed that zinc supplementation resulted in remarkably effective treatment of blepharospasm using the same botulinum toxin source and dosage that was ineffective in the same patient in the absence of supplementation.

The results surprisingly suggested that zinc deficiency sufficient to reduce the efficacy of administered botulinum toxin occurs in a significant number of patients. Even in those patients without overt resistance, increasing zinc levels by oral administration for a period of time prior to a planned injection is expected to provide a normalative advantage in all patients. In particular, by administering zinc supplements to provide intracellular zinc available for binding and activation of botulinum toxin LC endopeptidase, the highest possible $Zn^{2+}$ dependent response can be obtained. In many patients who have been previously refractory to administered botulinum toxin, lower doses can be administered with reliable responses. While eating copious amounts of high zinc-containing animal protein for a period of time prior to a treatment with botulinum toxin may be effective in normalizing and augmenting botulinum toxin responsiveness, this solution is inconvenient, lacks standardization, and, over the long run, is incompatible with the dietary preferences of most individuals.

Thus, in one aspect of the advancement provided herein, oral zinc supplements are administered which supply the desired normalization and augmentation of zinc stores. In one aspect of the invention, one or more forms of inorganic and/or organic zinc are formulated in tablet or capsule form. In one aspect, the dosage of zinc for oral consumption is in a range of about 10 to 400 mg of elemental zinc daily. In other embodiments, the dosage of zinc is in range of about 30 to 50 mg of elemental zinc daily. In one embodiment, the dosage of zinc is about 50 mg of elemental zinc daily. In one embodiment of the invention, a dose pack is provided to a patient prior to a planned procedure including a zinc supplement and instructions for taking the supplement. As provided in the instructions, the patient is directed to begin zinc supplementation several days prior to administration of botulinum toxin. In one embodiment, the patient is instructed to increase zinc supplementation for 3 to 4 days in advance of toxin treatment as well as on the day of treatment. In one aspect, the instructions direct the avoidance of foods high in phytates during the zinc loading period.

Example 2

Zinc Supplementation Including Increased Absorption of Zinc by Phytase Administration Given the role of phytates in inhibiting zinc absorption, in one aspect of the invention, oral zinc absorption is increased by oral administration of phytases which hydrolyze phytic acids (inositol hexakisphosphate) and improve zinc oral absorption. Phytases are presently available in the nutriceutical market as dietary supplements designed to increase the absorption of divalent cations such as calcium, magnesium, iron and zinc. These divalent cations form insoluble complexes with plant phytic acids present in plant foods such as corn, corn by-products, legumes, soybeans and cereal grains, rendering them unavailable. Phytases are used as additives to animal feeds for the purpose of making phosphates available from phytic acid (inositol hexakisphosphate). Addition of phytase to animal feeds has been disclosed to be an advantage even in low phytate diets. See e.g. WO9949740, disclosing a low phytate feed composition containing phytase from *Aspergillus*. WO9830681 entitled “Phytase Combinations” discloses that a combination of at least two phytases having different position specificity is more efficient in releasing phytate phosphorous.

Two types of dietary phytases are presently available, those from cereal and those from microbial sources. Microbial sources include fermentation of fungi such as *Aspergillus niger* (Finase®, Alko Ltd., Finland) as well as bacterial fermentation. Phytase activity is determinable by a number of different assays that measure the amount of enzyme required to liberate a set quantity of inorganic phosphate from phytic acid per minute at defined temperatures and pH. Microbial phytases have a broader range of pH activity and have been shown to provide increased iron absorption in human studies compared with wheat phytase. In one such study, administration of 20,000 phytase units (PU) increased iron absorption by 14 to 26%. See Sandberg A-S, et al. “Dietary *Aspergillus niger* Phytase Increase Iron Absorption in Humans” *The Journal of Nutrition* 126 (1996) 476. Thus, in one aspect a dietary supplement is provided that includes one or more forms of zinc and at least one microbial phytase. Administration of the zinc and the phytase prepare the patient for maximal responsiveness to the later administered botulinum toxin.

As mentioned above, zinc and phytase in combination may also be used to safely and effectively rapidly increase whole body zinc levels for applications other than improved binding and activation of botulinum toxin LC endopeptidase. For example, it may be desirable to increase whole body zinc levels in times of medical need, including, but not limited to, conditions such as: wound healing, burn recovery, immune compromise, and male impotency.

In order to further test the apparently positive results of dietary zinc supplementation provided by ingestion of a high zinc food, as well as to test whether addition of phytase would confer a benefit in zinc absorption, a further trial was initiated comparing reactivity to botulinum toxin in patients after a four day period of test supplementation with two different supplements compared with a placebo. Each of the test substances and the placebo were variously provided to the test subjects without identification. Thus, the patients were blinded to the nature of the supplement. The placebo (P) was a capsule form of lactulose. The two test preparations were $Z_{10}$, which was a normal RDA dose of 10 mg zinc in the form of zinc gluconate, and Z50P, which was a relatively high zinc loading dose providing 50 mg of zinc in the form of zinc citrate together with 3,000 PHU of phytase (derived from the fungus *Aspergillus niger*). Two different parameters of sensitivity to the botulinum toxin were recorded, duration (D) and effect (E). Duration was expressed as a percentage increase or decrease from the patient’s “usual” duration of effect because experience shows that different patients typically experience different effect durations. For some patients, toxin treatments typically last one month, for others three months, etc. So, a patient whose toxin usually lasts 90 days and for whom no change in duration was observed was scored as 0, i.e., no change from usual duration. A patient who experienced an additional 4 weeks (28 days) of toxin effect is calculated to have an increased duration of 28/90, the ratio of which equals +0.31 and representing an effect that is 31% longer than usual. Conversely, a negative score such as −0.25 equals an effect that is 25% shorter than usual. Effect (E) was expressed as deviation from the individual patient’s usual perception of comfort and desired effect. For example, 0=no change from usual effect, −1=slightly less effective than usual, −2=significantly less effective than usual, ±1=slightly more effective than usual, +2=significantly more effective than usual, +3=best effect ever achieved for that patient. To ensure accuracy, patients kept regular logs of perceived effectiveness of the treatment.

The results of a trial of 44 patients are presented in table form in FIG. 1. All of these patients had been treated previously and had a prior recorded history of botulinum toxin responsiveness. Twenty-three of the patients were considered to be hard-to-treat blepharospasm patients (BH), meaning they: a.) routinely required>50 units/session of Botox® brand BoNT-A or another botulinum toxin equivalence; b.) routinely had patient-reported suboptimal results despite maximized response from a customized injection dose and pattern; and c.) reported a degree of variability in toxin effect from treatment to treatment despite unchanging injection dose and pattern. A further seven patients were blepharospasm patients who consistently responded to BoNT-A treatment (BC). Four patients were hemifacial spasm (H) patients, while ten patients received cosmetic treatment for wrinkles (C). The three BoNT types administered are shown on FIG. 1 in the “T” columns as (“B”) BoNT-A (Botox®), (“M”) BoNT-B (Myobloc®), and ("D") BoNT-A (Dysport®). Patients were treated in a modified randomized, double-blind, placebo-controlled, crossover pilot study.

Study participants were unequally randomized to one of four treatment groups by a third party and both the treating physician and patients were blinded to the pre-injection supplements provided. Twenty-three (52%, group A) underwent pre-injection supplementation with $Z_{50P}$ alone (50 mg zinc citrate plus 3,000 units phytase), six (14%, group B) underwent pre-injection supplementation with both P (lactulose placebo) and $Z_{50P}$ at different times in a cross-over design, four (9%, group C) underwent pre-injection supplementation with $Z_{10}$ (10 mg zinc gluconate) and $Z_{50P}$ at different times in a cross-over design, and 11 (25%, group D) underwent study by pre-injection supplementation with P, $Z_{10}$, and $Z_{50P}$ at separate times in a triple cross-over design.

Referring now to FIG. 2, a graph 200 illustrating the results of the trial of supplementation of zinc and zinc plus phytase for four days prior to the administration of therapeutic botulinum toxins with respect to the duration (D) of the toxin's effect in the patient is shown. The vertical axis 202 in FIG. 2 represents the percentage change in the duration of the action of the toxin in the patient. The horizontal axis 204 shows various bars, each representative of a patient population receiving either: a placebo (P) 206; 10 mg of zinc gluconate ($Z_{10}$) 210; or 50 mg of zinc citrate in addition to phytase ($Z_{50P}$) 214. Confidence interval bars 208/212/216 represent 95% confidence intervals from the mean. As can be seen in FIGS. 1 and 2, no significant ($p>0.05$) change from usual, patient-specific treatment duration was seen in the duration (D) of botulinum toxin treatments with pre-injection supplementation for patients receiving either placebo (P) 206 or 10 mg of zinc gluconate ($Z_{10}$) 210, which approximates the RDA for zinc.

Figure 3:
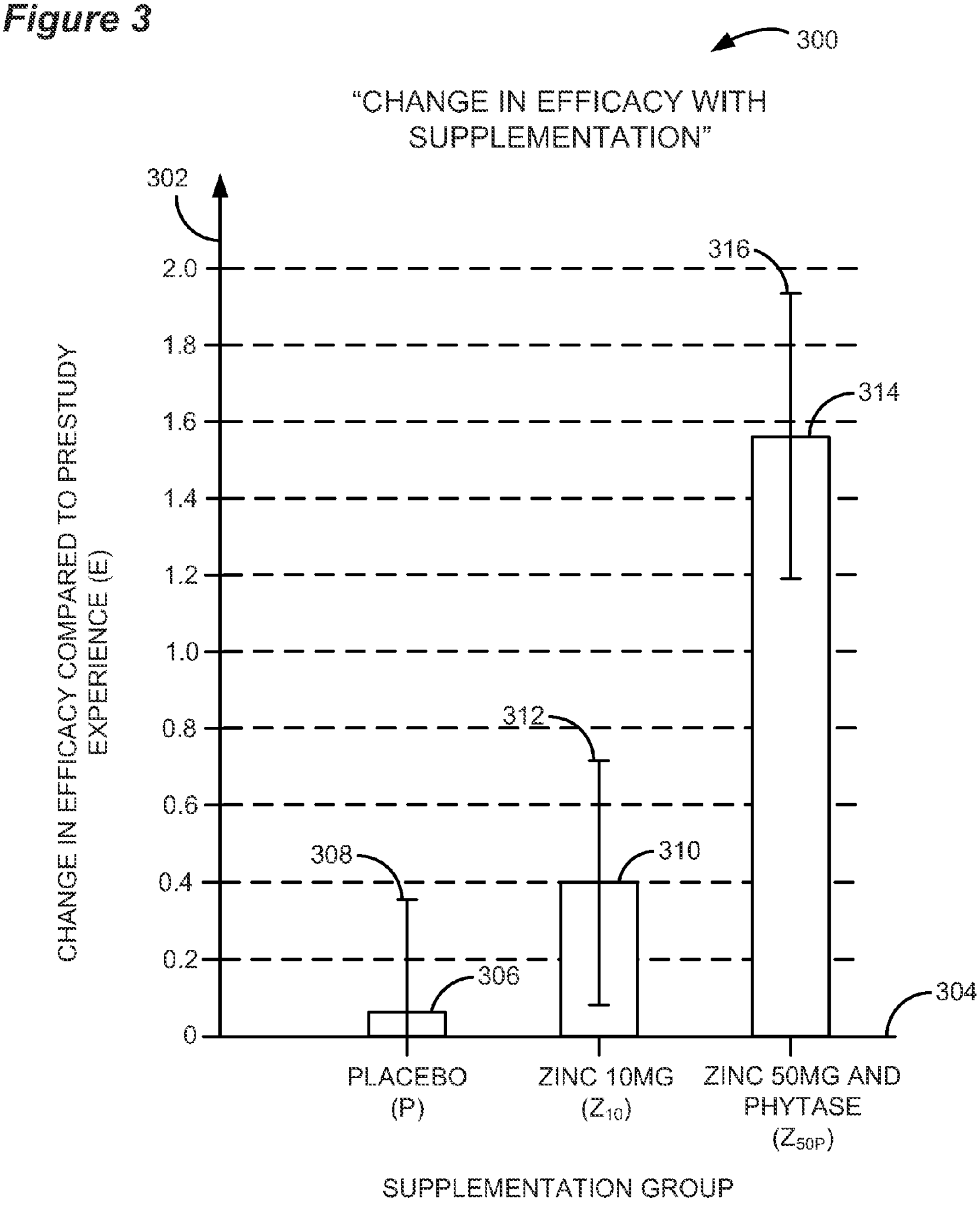
FIG. 3 depicts the graphic results of the trial of supplementation of zinc and zinc plus phytase for four days prior to administration of therapeutic botulinum toxins with respect to the patients' subjective perceived change in the efficacy of the toxin treatments.

Referring now to FIG. 3, a graph 300 illustrating the results of the trial of supplementation of zinc and zinc plus phytase for four days prior to the administration of therapeutic botulinum toxins with respect to the patients' subjective perceived change in the efficacy (E) of the toxin treatments is shown. The vertical axis 302 in FIG. 3 represents the perceived change in the efficacy (E) of the toxin in the patient. The horizontal axis 304 shows various bars, each representative of a patient population receiving either: a placebo (P) 306; 10 mg of zinc gluconate ($Z_{10}$) 310; or 50 mg of zinc citrate in addition to phytase ($Z_{50P}$) 314. Confidence interval bars 308/312/316 represent 95% confidence intervals from the mean. As can be seen in FIGS. 1 and 3, no significant ($p>0.05$) changes in effect (E) from patient-specific normal responsiveness were observed in the patients receiving either placebo (P) 306 or 10 mg of zinc gluconate ($Z_{10}$) 310, which approximates the RDA for zinc.

By contrast, in 41 of the 44 (93%) patients given $Z_{50P}$ (zinc citrate 50 mg plus 3,000 units phytase supplements) 214 for four days prior to botulinum injections, a patient-specific average increase in effect duration (D) of 23.6% was observed ($p<0.05$, See FIGS. 1 and 2). Further, in 38 of 44 patients (86%) given $Z_{50P}$ (zinc citrate 50 mg plus 3,000 units phytase supplements) 314 for four days prior to botulinum injections, the effect (E) of the botulinum toxin treatment was found to be increased significantly ($p<0.05$, See FIGS. 1 and 3). Virtually every patient showed improvement in duration (D), effect (E), or both. In most cases, both duration (D) and effect (E) were remarkably improved. In fact, in three blepharospasm patients given high zinc loading and phytase ($Z_{50P}$) who reported decreased beneficial effect, obvious toxin overdose was observed, making it difficult for them to close their eyes. Thus, even among these three patients, there was an increase in toxin effect. Among other things, the results suggested (and subsequent experience has shown) that lowered doses of BoNT can be administered with reasonable responsiveness in many patients if the patients are zinc loaded prior to treatment. By zinc loading prior to administration, maximum responsiveness can be normalized across the patient population, and one important variable in individual responsiveness can be eliminated. Lower effective doses may reduce the subsequent development of antibodies that interfere with treatment. This data is felt to be highly reliable, as blepharospasm patients are keenly aware on a daily basis whether or not they can keep their eyes open to function to read, drive, dress themselves, watch TV, work, shop, etc.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

The invention claimed is:

1. A pre-procedure therapeutic metalloprotease prep pack comprising:

a quantity of metal ion supplements in capsule or tablet form, wherein the supplements contain at least one metal ion determined to be required for activity of a therapeutic metalloprotease and wherein the supplements are provided in a quantity sufficient to supply the metal ion daily for a loading period immediately prior to treatment of a patient with the therapeutic metalloprotease;

a quantity of phytase supplements in powder, liquid, liquid-gel, capsule or tablet form, wherein the phytase supplements are provided in sufficient quantity for co-administration together with the metal ion supplements throughout the loading period;

and instructions directing the patient to take the metal ion supplements and reduce intake of phytates for a loading period immediately prior to treatment of the patient with the therapeutic metalloprotease.

2. The pre-procedure therapeutic metalloprotease prep pack of claim 1, wherein the quantity of phytase supplements provides 0.8 to 10,000 units of phytase to the patient daily.

3. The pre-procedure therapeutic metalloprotease prep pack of claim 1, wherein the therapeutic metalloprotease is a Clostridial neurotoxin.

4. The pre-procedure therapeutic metalloprotease prep pack of claim 3, wherein the metal ion supplement comprises an organic or inorganic form of zinc at a dosage sufficient to supply 10 to 400 mg of elemental zinc daily for a loading period immediately prior to treatment of the patient with the Clostridial neurotoxin.

5. The pre-procedure prep pack of claim 1, wherein the loading period is at least 4 days immediately prior to treatment of the patient with the therapeutic metalloprotease.

6. The pre-procedure prep pack of claim 1, wherein the loading period is less than 4 days immediately prior to treatment of the patient with the therapeutic metalloprotease.

7. A plurality of supplements provided to a patient to prepare the patient for treatment with a metalloprotease, wherein the supplements comprise:

a quantity of metal ions wherein the metal ions are required for activity of the metalloprotease and wherein the metal ions are provided in a quantity sufficient to supply the metal ions daily for a loading period immediately prior to treatment of the patient with the therapeutic metalloprotease and thereby eliminate a functional deficiency of the metal ions as a cause for poor or limited responsiveness to the administered therapeutic metalloprotease; and a quantity of phytase in powder, liquid, liquid-gel, capsule or tablet form, wherein the phytase is provided in sufficient quantity for daily co-administration together with the metal ions throughout the loading period.

8. The plurality of supplements of claim 7, wherein the therapeutic metalloprotease is a Clostridial neurotoxin.

9. The plurality of supplements of claim 8, wherein the quantity of metal ions comprises a quantity of an organic or inorganic form of zinc at a dosage sufficient to supply 10 to 400 mg of elemental zinc daily for a loading period immediately prior to treatment of the patient with the Clostridial neurotoxin.

10. The plurality of supplements of claim 7, wherein the loading period is at least 4 days immediately prior to treatment of the patient with the therapeutic metalloprotease.

11. The plurality of supplements of claim 7, wherein the loading period is less than 4 days immediately prior to treatment of the patient with the therapeutic metalloprotease.

12. A supplementation for use in a preparing a patient for enhanced response to administration of a botulinum toxin comprising:

a plurality of zinc supplements that are provided with instructions to the patient to consume the zinc supplements for a loading period prior to administration of the botulinum toxin, wherein the zinc supplements are provided in sufficient quantity to increase or maximize responsiveness to the botulinum toxin and eliminate a functional deficiency of zinc as a cause for poor or limited responsiveness to the administered botulinum toxin; and a plurality of phytase containing supplements in sufficient quantity for daily co-administration together with the plurality of zinc supplements throughout the loading period.

13. The supplementation of claim 12, wherein the zinc supplements include one or more forms of organic zinc and the zinc supplements deliver from 10 to 400 mg daily of elemental zinc.

14. The supplementation of claim 12, wherein the plurality of zinc supplements comprise an organic zinc form selected from one or more of: zinc proteinates, zinc chelates and/or salts with organic molecules, and zinc amino acid complexes.

15. The supplementation of claim 12, wherein the plurality of phytase containing supplements provide phytase supplementation at a level of 0.8 to 10,000 units daily.

16. The supplementation of claim 12, wherein the plurality of zinc and phytase supplements are supplements are provided in a quantity of up to and including 4 days of daily supplementation.

17. A kit suitable for preparing a patient for enhanced response to administration of a botulinum toxin comprising:

a quantity of zinc supplements provided in sufficient quantity to increase or maximize responsiveness to the botulinum toxin and eliminate a functional deficiency of zinc as a cause for poor or limited responsiveness to the administered botulinum toxin;

a quantity of phytase containing supplements in sufficient quantity for daily co-administration together with the plurality of zinc supplements throughout the loading period;

instructions for ingesting the quantity of zinc supplements during a loading period prior to administration of the botulinum toxin; and instructions to reduce intake of phytates during the loading period.

* * * * *